United States Patent [19]

Kirchgeorg et al.

[11] Patent Number: 5,771,513
[45] Date of Patent: Jun. 30, 1998

[54] X-RAY COMPATIBLE, PARTIALLY FLEXIBLE PATIENT SUPPORT

[75] Inventors: Markus Kirchgeorg, Schondorf; Ulrich Baer, Neunkirchen, both of Germany; James Bradcovich, Akron, Ohio

[73] Assignee: Beta Medical Products, Inc., Akron, Ohio

[21] Appl. No.: 657,208

[22] Filed: Jun. 3, 1996

[51] Int. Cl.⁶ .................................................. A47B 1/00
[52] U.S. Cl. .......................... 5/625; 5/628; 5/81.1 HS; 5/601; 428/902; 428/298.1; 428/299.1; 442/197; 128/870
[58] Field of Search ................. 5/81.1 R, 81.1 HS, 5/625, 628, 926, 601, 637; 428/902, 298.1, 299.1; 442/179; 128/870

[56] References Cited

U.S. PATENT DOCUMENTS

| | | | |
|---|---|---|---|
| 3,151,343 | 10/1964 | McCormick | 5/628 |
| 3,158,875 | 12/1964 | Fletcher | 5/628 |
| 4,067,079 | 1/1978 | Buchman | 5/81.1 R |
| 4,566,445 | 1/1986 | Jelsma | 5/628 |
| 4,640,275 | 2/1987 | Buzzese | 5/637 |
| 4,669,106 | 5/1987 | Ammerman | 128/870 |
| 4,895,173 | 1/1990 | Brault | 128/870 |
| 4,912,787 | 4/1990 | Bradcovich . | |
| 4,956,885 | 9/1990 | Alich et al. . | |
| 4,978,999 | 12/1990 | Frankel | 428/298.1 |
| 5,045,388 | 9/1991 | Bice | 428/299.1 |
| 5,121,514 | 6/1992 | Rosane . | |
| 5,230,112 | 7/1993 | Harrawood et al. . | |
| 5,271,110 | 12/1993 | Newman . | |
| 5,473,784 | 12/1995 | Nixon et al. . | |
| 5,474,362 | 12/1995 | Albecker, III . | |

FOREIGN PATENT DOCUMENTS

| | | | |
|---|---|---|---|
| 468336 | 7/1937 | United Kingdom | 5/625 |
| 09039 | 10/1989 | WIPO | 5/628 |

*Primary Examiner*—Flemming Saether
*Attorney, Agent, or Firm*—Oldham & Oldham Co., LPA

[57] ABSTRACT

A patient support fashioned of a core of carbon-fiber material and a synthetic material for binding the carbon-fiber material. The carbon-fiber core has a greater proportion of carbon fibers oriented substantially in lengthwise directions than in other directions. As a result of this construction, the patient support is substantially inflexible along its longitudinal axis yet flexible along its lateral axis. The sides of the support can be drawn up and around the patient, to hold the patient immobile within the support, which is especially helpful when transporting trauma patients and those with back and neck injuries. The support is also transparent to radiation, making it particularly suited to use with radiation imaging devices. Finally, the exterior surface of the support is formed of low-friction material, further facilitating practical use thereof. The support can be fashioned as a backboard or a patient transfer device and has a wide range of advantageous applications in a hospital environment.

39 Claims, 3 Drawing Sheets

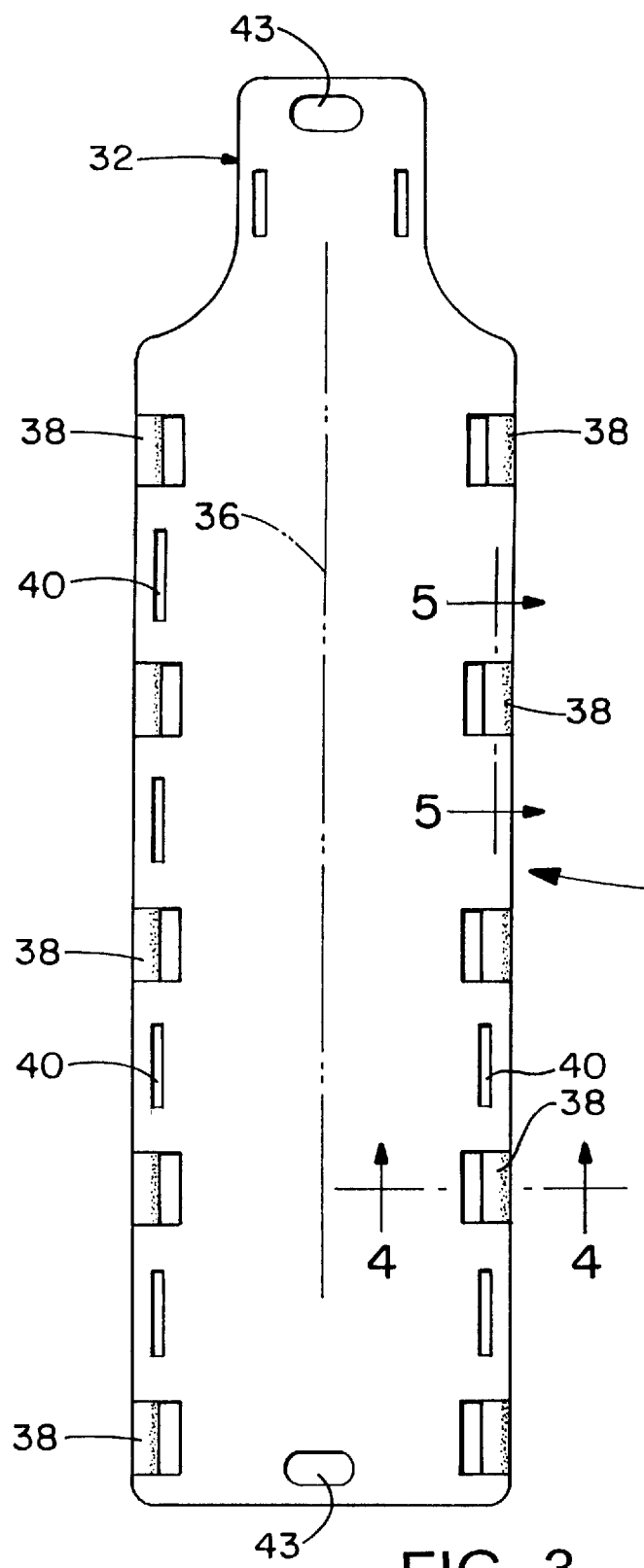
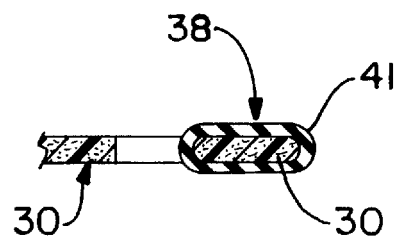
FIG.-4
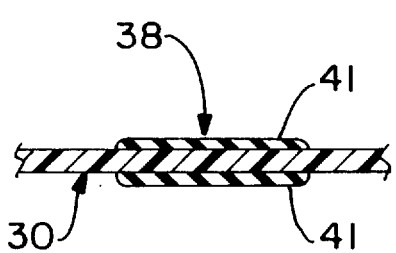
FIG.-5
FIG.-3

X-RAY COMPATIBLE, PARTIALLY FLEXIBLE PATIENT SUPPORT

FIELD OF THE INVENTION

The present invention relates to devices for supporting and moving patients, such as backboards and patient transfer devices. The invention further relates to methods for moving patients utilizing such devices. More particularly, the invention relates to such devices which are flexible along a lateral axis yet rigid along a longitudinal axis, and which are largely transparent to radiation.

BACKGROUND OF THE INVENTION

Devices known in the art for supporting and moving patients range from completely flexible sheets to entirely rigid boards and cots. Each of these extremes is associated with certain advantages as well as with certain disadvantages.

For instance, cloth sheets, which are still commonly used by medical personnel for moving patients back and forth between trolleys, beds and examining tables, have advantages in that they are lightweight and compact. However, it can be unwieldy to move a patient wrapped in a cloth sheet, especially if the patient is heavy. This causes inconvenience and overexertion and can in fact result in injuries to hospital personnel. Also, using sheets can be hazardous to the patients, in particular to patients with back and neck injuries, since sheets provide very little support and are not sufficiently secure.

Boards, stretchers and cots overcome the problems mentioned above, but, on the other hand, suffer from the disadvantages of being completely inflexible and often heavy. In addition, rigid devices are generally incompatible with radiation imaging devices. In the case of wooden boards, screws, voids and imperfections in the wood distort and detrimentally affect the radiation image. Similarly, molded fiberglass backboards have high x-ray absorption characteristics. Accordingly, patients transported to the imaging apparatus with such devices must be lifted from the device and transferred to the imaging table by some other means, or the devices must be removed from underneath the patients prior to imaging, since the devices cannot remain in the imaging path during x-ray imaging.

In addition, the surfaces of many of the devices discussed above have relatively high coefficients of friction, making it difficult to slide these devices onto or off of examining tables, trolleys and beds. For example, molded urethane backboards can exhibit relatively high coefficients of friction. Teflon boards, which have a coefficient of friction of about 0.15, have been proposed as one solution to this problem. However, teflon boards also have drawbacks, for example in that they are more flexible than desired and thus allow the patient's body to bend, potentially compounding injuries such as back and neck injuries.

Accordingly, there still exists a need in the art for devices for supporting and moving patients in a safe, efficient and controlled manner. In particular, devices for trauma patients or those with neck or back injuries could be improved. Further, there remains a need in the art for devices of this kind which are not only compatible with radiation imaging equipment but also are at least somewhat rigid.

Publications describing backboards, patient transfer devices and the like include U.S. Pat. Nos. to Alich et al. (4,956,885), Rosane (5,121,514), Harrawood et al. (5,230,112), Newman (5,271,110), and Nixon et al. (5,473,784).

OBJECTS OF THE INVENTION

One object, therefore, of the invention is to provide improvements in devices for supporting and moving patients. Another object is providing means and methods for more safely and securely moving patients, e.g., transferring patients from one surface to another. Yet another object of the invention is to provide a backboard or patient transfer device having a low x-ray absorption characteristic. A further object is providing devices for moving patients that have one or more surfaces characterized by a low coefficient of friction.

SUMMARY OF THE INVENTION

These and other objects are addressed and solved by the present invention in its various embodiments. In accordance with one aspect of the invention, the Applicants propose a device for moving a patient that has a support structure extending in a lengthwise direction. The support structure is fashioned of a core of carbon-fiber material and a synthetic material in which the carbon-fiber material is bound, i.e., suspended. The carbon-fiber core has a greater proportion of carbon fibers oriented substantially in the lengthwise direction than in other directions.

The invention further relates to a patient transfer device having a sheet for supporting the patient. The sheet is substantially inflexible along a longitudinal axis thereof yet flexible along a lateral axis thereof. The sheet is further required to be substantially transparent to radiation.

The invention also encompasses a backboard formed of a sheet of material supporting an object. The sheet defines a longitudinal axis and a lateral axis, and the object extends predominantly along the longitudinal axis. The sheet is flexible along the lateral axis thereof so as to curve about the longitudinal axis and partially around the object when supporting the object. The sheet is, however, rigid along the longitudinal axis when the sheet is supporting the object. Finally, the sheet is substantially transparent to radiation.

According to another aspect of the invention, a method is proposed for moving a patient from a patient transport to an examining table of an imaging apparatus and for performing an imaging operation. The steps involved in the method include: (i) placing a patient transfer device under the patient, the transfer device being substantially inflexible along a longitudinal axis thereof yet flexible along a lateral axis thereof, the transfer device further being substantially transparent to radiation; (ii) placing the patient transport, on which the patient is lying, proximate to the examining table; (iii) moving the patient from the patient transport to the examining table by means of the transfer device and positioning the transfer device and the patient on the examining table without removing the transfer device; and (iv) using the imaging apparatus to perform the imaging operation while the patient is lying on the transfer device and the transfer device is lying on the examining table.

A method for manufacturing a patient support structure is also encompassed by the present invention. This method has at least the following steps: (i) stacking a plurality of carbon-fiber sheets such that carbon fiber chains of the carbon-fiber sheets extend predominantly in directions forming acute angles relative to a longitudinal axis; (ii) covering the plurality of sheets from at least one side with at least one carbon fiber mat; (iii) bringing the covered sheets into contact with a synthetic polymer material; (iv) subjecting the contacted, covered sheets to a heat and pressure treatment that causes the synthetic polymer material to bind with the covered sheets, to thereby form the support structure.

BRIEF DESCRIPTION OF DRAWINGS

FIG. 3 is a plan view of a patient support according to a second embodiment of the invention.

FIG. 4 shows a partial cross-section of the support illustrated in FIG. 3, taken along the line 4—4.

FIG. 5 shows another partial cross-section of the support illustrated in FIG. 3, taken along the line 5—5.

DETAILED DESCRIPTION OF THE PREFERRED EMBODIMENTS

Figure 1:
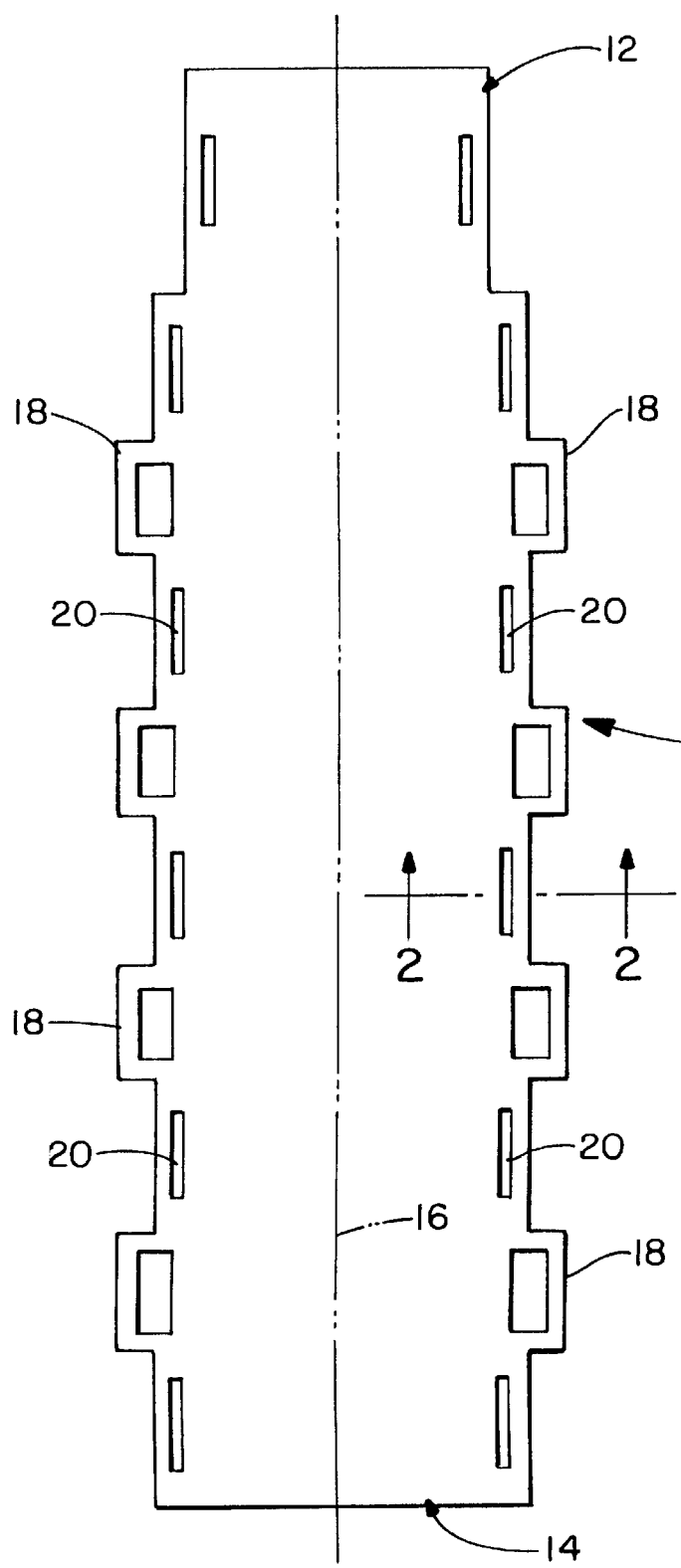
FIG. 1 is a plan view of a patient support according to a first embodiment of the invention.

FIG. 1 shows a patient support in plan view, designated generally by reference numeral 10. The patient support in this embodiment is formed as a generally unitary support sheet or structure. The support 10 is longer in the lengthwise direction, which extends from a head end portion 12 of the support 10 to a base end portion 14 along a longitudinal axis 16. The support 10 is dimensioned so as to be able to support the body of a patient. For example, as illustrated, the support may have a generally rectangular shape. Preferably, the support measures approximately 2 meters in length and about 0.5 meters across at its widest points. The head end 12 is preferably somewhat narrower, e.g., 0.4 meters.

A plurality of handholds 18 are provided along the sides of the support 10 at regular intervals, so as to be symmetrical with respect to the longitudinal axis 16. The handholds 18 are formed by roughly rectangular holes extending through the support 10 and by peripheral areas of the support lying laterally outward from the holes. In this embodiment, the handholds 18 jut out slightly from the sides of the support 10 even though they are integral with and composed of the same material as the support.

In addition to the handholds 18, the sides of the support 10 have slit-like openings 20 for securing patient restraint loops (not shown in FIG. 1). In the embodiment of FIG. 1, these openings 20 alternate with the handholds 18, except at the head end portion 12 of the support 10.

FIG. 2 is a partial cross-section of a patient support 11, e.g., a patient support fashioned such as the one illustrated in FIG. 1. The overall thickness of the support 11 is preferably less than 5 millimeters, e.g., 3 mm.

Reference numeral 22 designates a core of carbon-fiber material. Carbon fibers are high-tensile, extremely stiff fibers having diameters of roughly 8 microns, which can be aligned to form carbon fiber chains. According to the invention, the carbon fiber core 22 has a relatively large proportion of its carbon fibers oriented substantially in the lengthwise directions of the support. In other words, the carbon fibers point generally in the direction of the head end and base end of the support. It is not necessary, however, that all or nearly all carbon fibers be oriented in the lengthwise directions. However, preferably, more than three quarters by volume of the carbon fibers are oriented substantially in the lengthwise direction.

In addition, the carbon fibers should not all be aligned exactly with the longitudinal axis. While some carbon fibers may extend parallel to the axis, other fibers should be oriented simply at acute angles to the longitudinal axis, e.g., in the range of 5°–10°. Thus, according to one preferred embodiment, in preparing the carbon fiber core, carbon fiber material is laid in such a manner that roughly three quarters or more of the carbon fibers by volume are oriented to be off-axis by less than 10°. The remaining fibers are preferably randomly oriented in directions other than substantially in the lengthwise direction.

Figure 2A:
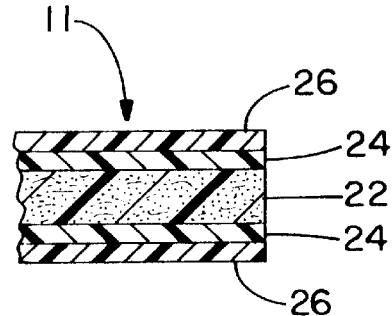
FIG. 2A shows a patient support in partial cross-section, to illustrate the composition of the patient support resulting from a first method of manufacture.

In the FIG. 2A embodiment, layers 24 bind the carbon fiber core 22 from both sides. The material forming layers 24 preferably is bound into the core and around the carbon fibers and can be polyurethane, polypropylene, teflon or the like. A layer 26 forming the outermost layer on both surfaces is selected to yield a low coefficient of friction. Polypropylene, which has a coefficient of friction of roughly 0.15, is the preferred material for layer 26.

Figure 2B:
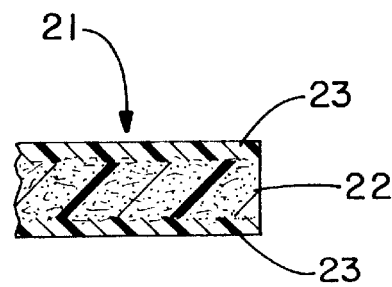
FIG. 2B shows a patient support in partial cross-section, to illustrate the composition of the patient support resulting from an alternate method of manufacture.

An alternate composition for a support 21 is illustrated by the partial cross-sectional view of FIG. 2B, where reference numeral 22 again indicates a carbon fiber core. According to the FIG. 2B embodiment, the intermediate layer 24 is omitted. Instead, an outer layer 23, preferably polypropylene, is bonded directly to the carbon fiber core 22. As in the previous embodiment, the polypropylene layer 23 provides an outer layer having a very low coefficient of friction, which facilitates moving the support easily across surfaces such as examining tables, etc.

In FIGS. 2A–2B, layers 23, 24 and 26 all constitute synthetic materials in which the carbon fiber core 22 is suspended. As such, both figures illustrate examples of carbon-fiber reinforced synthetic materials. The synthetic material layers should preferably coat the carbon fiber core 22 entirely from at least one side.

In both FIGS. 2A and 2B, the supports 11, 21 are symmetrical in that layers 23, 24 and 26 are formed on both sides of the core 22. This renders the supports particularly versatile, since they thereby become reversible. If this characteristic is not desired, however, it is also feasible to form the supports 11, 21 with synthetic material layers and/or low friction layers on only one side of the support.

The carbon-fiber core 22 preferably has a thickness between approximately 1.0 mm and 1.5 mm. This thickness produces a structure that is capable of supporting an adult having a mass of up to 200 kg. In addition, as will be explained further below, this thickness provides a support with very low x-ray absorption characteristics, which is therefore x-ray compatible. The indicated thickness of the core 22 also allows the support to be as thin as 2–5 mm overall, which greatly facilitates moving patients on and off the support, since the support can be slid under the patient with relative ease.

A support having the composition according to one of the embodiments just described can be manufactured as follows. In order to provide the carbon fiber core 22, a plurality of carbon-fiber sheets are stacked in such a manner that the carbon-fiber chains in those sheets are oriented at acute angles relative to a set axis. The number of sheets used is determined largely in inverse relation to the section modulus of the individual sheets, with the strength properties desired in the finished product guiding the appropriate balance between sheet number and section modulus. Various alternatives are available for the carbon-fiber sheets. These include carbon fiber cloth, which is a loose mat of carbon fiber, or carbon-fiber pre-preg, which is carbon fiber impregnated with a synthetic resin. Regarding the orientation of the mats, it is preferable to have the carbon-fiber chains form angles within ±5° to ±10° of the set axis, with some mats oriented to the − side and others to the + side of the axis. Once the carbon-fiber sheets, e.g., three to five sheets, have been appropriately oriented and laid, the stack of carbon-fiber sheets is sandwiched between a carbon-fiber mesh, for stability.

The resulting stack is then treated with a synthetic polymer material, such as polyurethane, urethane or polypropylene. This can be accomplished by spraying or coating the stack with the polymer material, by laying the stack between polypropylene pre-preg sheets, by setting the stack in a fluid sheet of polypropylene, etc. This laminate is then subjected to a heat and pressure treatment, in, e.g., a platten, autoclave or the like, for the purpose of binding the polymer material into and onto the carbon fiber core. The heat and pressure should be sufficiently high to bring the polymer layers to their phase point and bind them into and onto the carbon-fiber core. In addition, the heat and pressure can be varied, e.g., by using several different plattens, in order to achieve desired bonding characteristics and surface finishes for the support.

By way of example, pressures of roughly 500 PSI and temperatures of roughly 400° F. can be used to melt and bind polypropylene outer layers 23 into and onto the core 22, to form the support 21 illustrated in FIG. 2B. If the polymer layer used in the above procedure does not have a sufficiently low coefficient of friction, then the support can thereafter be coated with low-friction material, e.g., polypropylene, to form a support 11 as illustrated in FIG. 2A.

The composition of the supports according to the embodiments described above, along with the orientation of the carbon fiber chains in the core and the other parameters as described, produce a patient support with several highly desirable characteristics and features.

First, the resulting patient support exhibits a nonisotropic flexibility characteristic. The support is relatively flexible across its width, allowing the sides to be bent up and down from their rest position in the plane of the support to form, e.g., an arcuate or parabolic cross-section. Accordingly, when a patient is lying on the support 10 and the support is lifted by the handholds 18, the weight of the patient will cause the support to bow visibly under the weight of the patient and to curve around the patient. Since the support conforms to the shape of the patient and at least partially envelops the patient, the patient is held secure within the support.

The flexibility of the support is determined in accordance with design specifications through appropriate selection of, e.g., the orientation of carbon fiber chains, the relative proportions of carbon fibers pointing in the various directions relative to the longitudinal axis, the thickness of the carbon fiber core 22, and the thickness and composition of the synthetic material layers in which the carbon fibers are suspended. A support that curves generously around the patient and is capable of forming at least a semi-circle in cross section has been found to be particularly advantageous.

Figure 8:
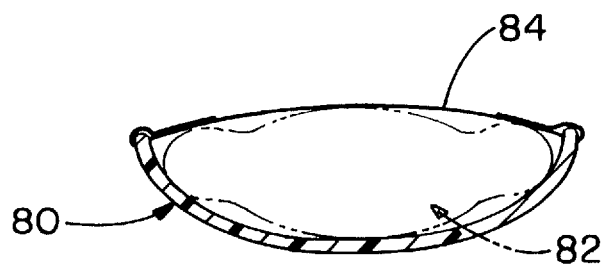
FIG. 8 shows, in cross-section, a support curved about a patient and secured by means of restraining loops.

The support can also be caused to curve around the patient through the use of patient restraint loops. FIG. 8 illustrates this situation by way of a cross-sectional diagram of a patient 82 lying on a support 80. Restraint loops 84 affixed to the support 80 at opposing locations along the edges of the support are pulled taught, so that the support 80 curves around the patient 82 and conforms roughly to the girth of the patient. As a result, the patient is held firmly within the confines of the support and can be safely and securely transferred from one location to another.

As noted above, however, the flexibility of the support is anisotropic. In the longitudinal direction, the support is much stiffer than in the lateral direction. As explained above, this is caused by the orientation of the carbon fiber chains of the core of the support in relation to the longitudinal axis. Given this non-isotropic flexibility property, it is more difficult to bend the ends of the support up and down from their planar rest position than to bend the sides up and down.

While the composition and manufacture of the support renders the support substantially more stiff in the longitudinal direction than in the lateral direction, the rigidity in the longitudinal direction is further enhanced when the support is not laying flat but rather is curved around a patient as described above. In other words, when the support is bent laterally and takes on a trough-like shape, the support becomes extremely stiff in the longitudinal direction, such that the normal weight of a patient is insufficient for flexing the support in the longitudinal direction. Accordingly, when a patient is lying on the support 10 and the support is curved around the patient, e.g., as illustrated in FIG. 8, the support will remain substantially rigid in the longitudinal direction. As discussed under the heading "Background of the Invention", above, such rigidity is very useful and desirable for supporting and moving trauma patients and patients with back and neck injuries in particular. The firm, rigid support provided by the support according to the invention allows such patients to be transferred and positioned safely and securely, with minimal risk that their injuries will be aggravated.

A second desirable and beneficial characteristic of these supports is their radiation permeability. A support according to the embodiments described above can be manufactured to have a radiation absorption of less than 1 mm aluminum equivalent, well below the DHHS radiation performance standard of 1.5 mm under 21 C.F.R. Subchapter J, rendering it acceptable for use as a mobile device during radiation imaging procedures. Indeed, the support also meets the performance standard of 1.0 mm for fixed tables under 21 C.F.R. Subchaper J. More specifically, radiation absorption ranges as low as 0.25 mm–0.3 mm aluminum equivalent can be achieved without compromising other beneficial characteristics, such as the anisotropic flexibility of the support, etc.

As a result, a patient being transferred to the table of an imaging device, such as a computer tomography device, flat film x-ray device, nuclear imaging device, or digital radiographic device (e.g., fluoroscopic imager), need not be removed from the support. Nor does the support have to be extracted from underneath the patient prior to imaging. Instead, the support can remain under the patient, or even curved around the patient, during the imaging operation. The support can thus be used to transfer the patient safely and securely onto and off of the imaging table with great efficiency and minimum inconvenience.

Third, the low-friction outer layer or layers of the support and the slender profile of the support further enhance the ease and efficiency with which patients can be moved and transferred from one surface to another. As noted above, the thinness of the support allows it to be brought underneath the patient readily. The slickness of the surface allows it to be positioned by sliding as well as by actually lifting and setting down the support. Of course, as already mentioned, the longitudinal rigidity of the support renders lifting and setting straightforward as well.

Using polypropylene as the outermost layer of the support achieves not only the low-friction benefit but further provides a surface that is durable. It has high resistance to chemicals such as cleaning and disinfecting agents. Finally, it is also able to withstand heat and pressure to a considerable degree. Alternate surface substances that exhibit much of the same properties and that could be used instead include teflon and nylon.

FIG. 3 shows a support, in plan view, that is structured and dimensioned somewhat differently than the support 10 illustrated in FIG. 1. The support 30 in FIG. 3 has a narrower head end 32, which conforms more closely to the size of the head of a typical adult patient. The width of the head end 32 is, for example, 0.2 meters. Also, handholds 38 are arranged at different locations than as shown in FIG. 1 and are essentially flush with the side edges of the support 30. Finally, the handholds 38 are thicker in cross section than the interior of the support 30. This is done to render the handhold more comfortable to the persons lifting and moving the support 30. The handholds 38 may be composed of the same material as the support 30 and simply be molded to be thicker than the remainder of the support 30. Alternatively, as illustrated in FIGS. 4 and 5, the handholds may be cushioned with a polymer padding 41 encircling the peripheral areas. The polymer padding 41 may be selected from such materials as polyethylene, polypropylene or, preferably, rubber.

If desired, the handholds 18 or 38 can be supplemented with or replaced entirely by ropes or straps (not shown) attached to the support 10, 30. Such ropes or straps can be made, e.g., of nylon.

Additional holes 43 are provided at the top and bottom portions of the support 30. These additional holes can function either as additional handholds or as locations for securing the support 30 to a surface on which the support is resting.

Figure 6:
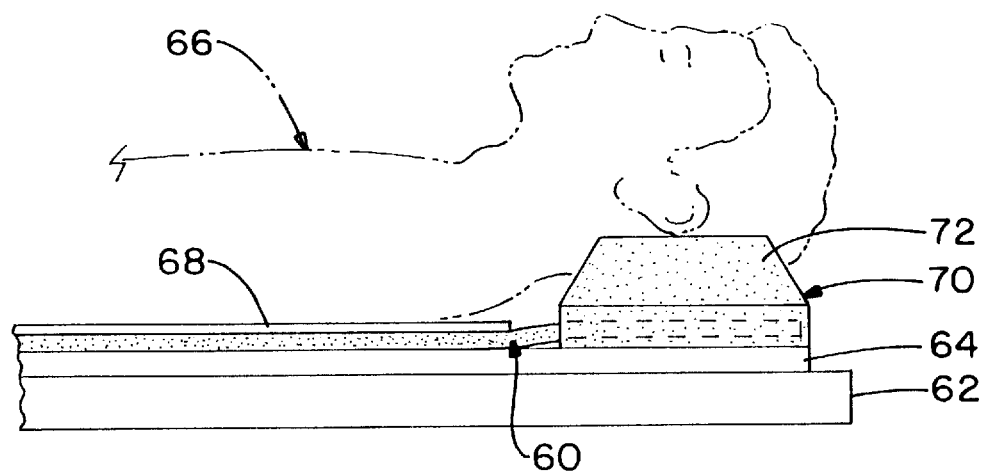
FIG. 6 is a partial side view of a patient support, according to a third embodiment of the invention, which includes a head rest at the upper end portion of the support and which is shown supporting a patient.

FIG. 6 illustrates yet another embodiment of the patient support. The patient support 60 is shown in partial side view, resting on a table 62 and a flat insert 64 of a computer tomography or other radiation imaging device. The remainder of the imaging device is not shown, but includes conventional components such as imaging equipment (e.g., a radiation source and detector), image processing equipment (e.g., electronic hardware and software, image developer equipment or the like), mechanical structures for holding and moving the table 62 and/or the imaging equipment (e.g., support structures, C-arms, motor drives, etc.) and so forth. A patient 66, e.g., trauma patient, is shown resting on the patient support 60. A mat 68 has been affixed onto the patient support, e.g., by VELCRO® straps. The mat 68 should of course be manufactured of a radiation-translucent material, since it, along with the patient support itself, will be in the radiation path during imaging.

In addition, the patient support 60 has a head rest 70 attached to the head end portion thereof. One embodiment of a suitable head rest is illustrated in side view in FIG. 6 and in cross-section in FIG. 7. This head rest 70 has a base portion 71 extending under and around the support 60 and two wall portions 72, 73 extending upward from the base portion 71. The walls 72, 73 are shown as being parallel to one another and perpendicular to the base portion 71 and the support 60, although this is not required. For example, the wall portions 72, 73 could be angled outward or inward from the perpendicular. A foam insert 74 is wedged or otherwise secured between the two wall portions 72, 73. This insert 74 preferably is hollowed to form depressions conforming to the shape of a patient's head, so that the head can be comfortably yet firmly positioned within the head rest.

Since the patient 66 preferably remains on the support 60 during a radiation imaging procedure, the entire head rest 70 is therefore best constructed of radiation-translucent material. The base portion 71 and the walls 72, 73 are preferably manufactured much like the patient support 60, with carbon-fiber reinforced synthetic material. The material for the foam should also be selected at least partly based on the permeability to radiation of the material.

Figure 7:
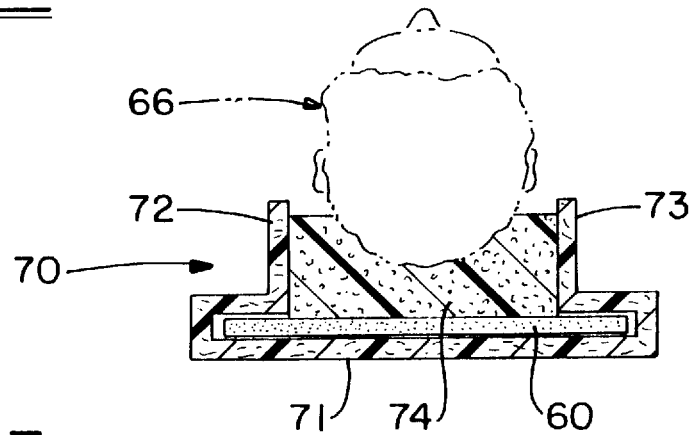
FIG. 7 is a view in cross-section of the patient support with head rest illustrated in FIG. 6.

The head rest 70 can be affixed to the support 60 in a variety of ways, but preferably attaches without the use of pins or screws. FIG. 7 shows one solution, in which the base portion 71 is designed to snugly embrace and grip the head end portion of the patient support 60. According to this design, the head rest 70 is mounted simply by sliding the base portion 71 over the head end portion of the patient support. The head rest 70 is then held in place by frictional contact between the inner walls of the head rest and the outer surface of the support 60 and by the clamping action of the head rest pressing against the support.

The patient support according to the invention can be utilized advantageously in a variety of settings and situations. For example, the patient support can be used as a backboard for lifting and moving a trauma patient from an accident scene to an ambulance. The inflexibility of the support along the longitudinal axis allows it to be used in lieu of other conventional backboards or stretchers. Additionally, since the patient support is very thin and relatively lightweight, it can remain under the patient in the ambulance while the patient is being transported to the hospital. The support can be secured within the ambulance by means of the handholds 18, 38, the additional holes 43, or some other appropriate means.

The patient support is particularly well suited to situations in which the patient's injuries could be aggravated through movement. The patient can be securely confined within the patient support enroute to the hospital through the use of the restraint loops 84 for pulling the support snuggly around the patient as illustrated in FIG. 8. The confining nature of the patient support when curved around the patient also helps to keep IV cords and the like properly in place. Use of a head rest 70 such as the one shown in FIGS. 6 and 7 provides further protection against movement of the head, neck and/or shoulders.

Once the patient arrives at the hospital, the patient support can be used either in conjunction with or in lieu of a trolley. If the support is used with a trolley, the patient, together with the patient support, is placed onto the trolley. If the patient did not arrive on a patient support, the support can be placed underneath the patient at this time. The thinness and the low-friction outer surface of the support renders this procedure easier than with many conventional devices. The patient is then wheeled to an appropriate destination within the hospital.

When the patient arrives at the destination, the trolley is placed next to or near, e.g., an examination table. Medical personnel then lift or slide the support onto the table. The slick underlayer of the support greatly facilitates this procedure as well. In many circumstances, the patient support can simply remain under the patient. This not only lessens the effort expended in the transfer procedure, but also renders the procedure very efficient, saving time that is potentially critical to the well-being of the patient. Since the outer surface of the patient support is robust and capable of being disinfected, it can be reused by the hospital.

Once the patient has been properly positioned on the examining table, examination and treatment of the patient can proceed. Depending on the nature of the injury and the examination, the patient support is either kept snugly fitted around the patient by the restraint loops or allowed to lay flat against the examining table. An added benefit of having the patient support be flexible along its lateral axis is that it is capable of conforming to the shape of the examining table, which is not always planar. For example, various types of imaging devices are designed as tubes and have curved surfaces for supporting the patient.

As has already been indicated, the inventive patient support is particularly suited to use in moving a patient to or from the examining table of a radiation imaging apparatus. Since the support is substantially transparent to radiation, it need not be removed from underneath the patient prior to carrying out the imaging procedure, unlike many conventional patient transfer devices. The radiation permeability of the support allows radiation to pass through the support without unduly affecting the resulting images.

Once the imaging procedure is completed, the support can again be used to move the patient to a further destination, e.g., another examination table, a hospital bed or the like.

While use of the patient stretcher has been described in particular in conjunction with radiation imaging equipment, it should be apparent from the discussion above that the patient support can be effectively utilized during other procedures, e.g., x-ray therapy, a variety of other diagnostic procedures (excluding, however, procedures that create strong electrical fields in the vicinity of the patient, since carbon-fiber is conductive), and even surgery.

The invention disclosed herein relates to patient supports fashioned of a core of carbon-fiber material and a synthetic material for binding the carbon-fiber material. The carbon-fiber core has a greater proportion of carbon fibers oriented substantially in lengthwise directions than in other directions. As a result of this construction, such patient supports are substantially inflexible along longitudinal axes thereof yet flexible along lateral axes thereof. The sides of these supports can be drawn up and around the patient, to hold the patient immobile within the support, which is especially helpful when transporting trauma patients and those with back and neck injuries. These supports are also transparent to radiation, making them particularly suited to use with radiation imaging devices. Finally, their exterior surface is formed of low-friction material, further facilitating practical use of these supports. They can be fashioned as backboards or patient transfer devices and have a wide range of advantageous applications in a hospital environment.

We claim:

1. A device for moving a patient, comprising:
   a support structure defining a lengthwise direction and comprising:
   a core of carbon-fiber material having a greater proportion of carbon fibers oriented substantially in the lengthwise direction than in directions other than the lengthwise direction; and
   a synthetic material in which said carbon-fiber material is suspended;
   wherein said support structure is flexible in a direction perpendicular to the lengthwise direction yet is relatively inflexible in the lengthwise direction, and wherein said support structure, when flexed to form a curve in cross section, is substantially rigid in the lengthwise direction.

2. The device according to claim 1, wherein greater than 75% of the carbon fibers by volume are oriented substantially in the lengthwise direction.

3. The device according to claim 1, wherein the greater proportion of carbon fibers is oriented at acute angles relative to a longitudinal axis extending in the lengthwise direction.

4. The device according to claim 3, wherein the greater proportion of carbon fibers is oriented at angles less than 10° relative to the longitudinal axis.

5. The device according to claim 1, wherein said support structure consists essentially of said synthetic material and said carbon-fiber core.

6. The device according to claim 1, wherein said support structure is manufactured from plural sheets of carbon-fiber pre-preg material.

7. The device according to claim 1, wherein said support structure is manufactured from plural sheets of carbon-fiber cloth material.

8. The device according to claim 1, wherein said support structure is radiation-permeable.

9. The device according to claim 8, wherein said support structure is substantially transparent to radiation.

10. The device according to claim 9, wherein said support structure is substantially transparent to X-rays.

11. The device according to claim 9, wherein said support structure has a radiation absorption of less than 1 mm aluminum equivalent.

12. The device according to claim 11, wherein said support structure has a radiation absorption between 0.25 mm and 0.35 mm aluminum equivalent.

13. The device according to claim 1, wherein said support structure is configured to support a patient having a mass of up to 200 kg.

14. The device according to claim 1, wherein said support structure has a thickness of less than 5 mm.

15. The device according to claim 1, wherein said support structure has a thickness of approximately 3 mm.

16. The device according to claim 1, wherein said carbon fiber core has a thickness between 1.0 mm and 1.5 mm.

17. The device according to claim 1, wherein said support structure measures approximately 2 meters in the lengthwise direction and approximately 0.5 meters in the perpendicular direction.

18. The device according to claim 1, wherein said synthetic material forms an outer layer of said support structure on at least one surface of said support structure and has a low coefficient of friction.

19. The device according to claim 18, wherein the coefficient of friction is less than 0.5.

20. The device according to claim 19, wherein the coefficient of friction is approximately 0.15.

21. The device according to claim 18, wherein said synthetic material having the low coefficient of friction consists essentially of polypropylene.

22. The device according to claim 18, wherein said synthetic material having the low coefficient of friction forms an outer layer of said support structure on both surfaces of said support structure, thereby rendering said support structure reversible.

23. The device according to claim 1, wherein said support structure further comprises:
   a surface layer having a low coefficient of friction and substantially covering said support structure on at least one surface of said support structure.

24. The device according to claim 23, wherein the coefficient of friction is less than 0.5.

25. The device according to claim 24, wherein the coefficient of friction is approximately 0.15.

26. The device according to claim 23, wherein said surface layer consists essentially of polypropylene.

27. The device according to claim 23, wherein said surface layer having the low coefficient of friction forms an outer layer of said support structure on both surfaces of said support structure, thereby rendering said support structure reversible.

28. The device according to claim 1, wherein handholds are provided at selected locations around a perimeter of said support structure.

29. The device according to claim 28, wherein said handholds are provided, respectively, by holes formed in said support structure and peripheral areas of said support structure adjacent said holes.

30. The device according to claim 29, wherein said peripheral areas are each thicker in cross section than is a central portion of said support structure in cross section, and have rounded edges.

31. The device according to claim 30, wherein said peripheral areas are rendered thicker in cross section by polymer padding covering each of said peripheral areas.

32. The device according to claim 1, wherein holes in said support structure for receiving patient restraint loops are provided at selected locations around a perimeter of said support structure.

33. The device according to claim 1, wherein said support structure has a head end portion and a central portion, the head end portion having a width, extending in the perpendicular direction, that is narrower than a width of the central portion.

34. The device according to claim 33, wherein the width of the head end portion measures between 0.2 meters and 0.4 meters, and the width of the central portion measures approximately 0.5 meters.

35. The device according to claim 1, further comprising:
   a head rest affixed to an end portion of said support structure.

36. The device according to claim 35, wherein said head rest comprises inner wall portions defining a slot for receiving and gripping the end portion of said support structure.

37. The device according to claim 35, wherein said head rest comprises two wall portions, which extend out from said sheet, and a foam insert extending between said wall portions and configured to receive and restrict lateral movement of a head of a patient being supported by said support structure.

38. The device according to claim 37, wherein said two wall portions and said foam insert are substantially transparent to radiation.

39. A method for manufacturing a patient support structure, comprising the steps of:
   stacking a plurality of carbon-fiber sheets such that carbon fiber chains of said carbon-fiber sheets extend predominantly in directions forming acute angles relative to a longitudinal axis;
   bringing the covered sheets into contact with a synthetic polymer material; and
   subjecting the contacted, covered sheets to a heat and pressure treatment causing the synthetic polymer material to bind with the covered sheets, to thereby form a support structure which is flexible in a direction perpendicular to said longitudinal axis yet is relatively inflexible in the direction of said longitudinal axis.

* * * * *